(12) United States Patent
Reddy et al.

(10) Patent No.: US 7,435,826 B2
(45) Date of Patent: Oct. 14, 2008

(54) SUBSTITUTED SULFOXIDES

(75) Inventors: Bandi Parthasaradhi Reddy, Hyderabad (IN); Kura Rathnakar Reddy, Hyderabad (IN); Raji Reddy, Hyderabad (IN); Dasari Muralidhara Reddy, Hyderabad (IN)

(73) Assignee: Hetero Drugs Limited, Hyderabad Andhrapradesh (IN)

( * ) Notice: Subject to any disclaimer, the term of this patent is extended or adjusted under 35 U.S.C. 154(b) by 0 days.

(21) Appl. No.: 11/620,843

(22) Filed: Jan. 8, 2007

(65) Prior Publication Data

US 2007/0129406 A1    Jun. 7, 2007

Related U.S. Application Data

(62) Division of application No. 10/503,830, filed as application No. PCT/IN2004/000118 on Aug. 6, 2004, now Pat. No. 7,176,319.

(51) Int. Cl.
*C07D 401/12* (2006.01)

(52) U.S. Cl. .................................................. 546/273.7

(58) Field of Classification Search ............... 546/273.7
See application file for complete search history.

(56) References Cited

U.S. PATENT DOCUMENTS

| 5,948,789 A | 9/1999 | Larsson et al. |
| 6,559,167 B1 | 5/2003 | Garst et al. |

FOREIGN PATENT DOCUMENTS

| DE | 4035455 | 5/1992 |
| EP | 0221041 | 5/1978 |
| EP | 0005129 | 4/1981 |
| WO | WO 94/27988 | 8/1994 |
| WO | WO 2004/002982 | 1/2004 |

OTHER PUBLICATIONS

Sigrist-Nelson K, Krasso A, Muller RK, Fischli AE. Ro 18-5364, a potent new inhibitor of the gastric (H+ + K+)-ATPase. Eur J Biochem. Jul. 15, 1987;166(2):453-9.

*Primary Examiner*—Patricia L Morris
(74) *Attorney, Agent, or Firm*—Caesar, Rivise, Bernstein, Cohen & Pokotilow, Ltd.

(57) ABSTRACT

The present invention relates to a process for preparing substituted sulfoxides either as a single enantiomer or in an enantiomerically enriched form. Thus, racemic omeprazole is reacted with (S)-camphorsulfonyl chloride to form a diastereomeric mixture and the diastereomers are separated by fractional crystallization, followed by deprotection to give esomeprazole.

5 Claims, No Drawings

SUBSTITUTED SULFOXIDES

This application is a Divisional of U.S. patent application No. 10/503,830, filed Aug. 6, 2004, the disclosure of which is hereby incorporated in its entirely.

FIELD OF THE INVENTION

The present invention relates to a process for preparing substituted sulfoxides either as a single enantiomer or in an enantiomerically enriched form.

BACKGROUND OF THE INVENTION

Substituted 2-(2-pyridinylmethylsulfinyl)-1H-benzimidazoles such as for example omeprazole, pantoprazole, lansoprazole and rabeprazole including their stereioisomers are inhibitors of gastric acid secretion. Omeprazole, chemically 5-methoxy-2-[[(4-methoxy-3,5-dimethyl-2-pyridinyl)methyl]sulfinyl]-1H-benzimidazole is for instant disclosed in EP 5129. Some compounds useful as prodrugs of proton pump inhibitors are disclosed in U.S. Pat. No. 6,559,167.

These compounds and structurally related compounds have a stereogenic center at sulfur and therefore exist as two optical isomers. The resolution processes of racemates of these compounds were for example disclosed in DE 4035455 and WO 94/27988. According to these processes chiral ether such as fenchyloxymethyl or chiral acyloxy methyl group such as mandeloyl- is introduced into the 1-position of benzimidazole ring of racemic sulfoxide compound to obtain a diastereomeric mixture, diastereomers are then separated and desired isomer is liberated from a separated diastereomer. The process requires either the preparation of fenchyloxymethyl chloride and then reaction with the racemic compound; or introduction of chloromethyl group on 1-position of benzimidazole ring, followed by reaction with the chiral auxiliary. We find that these intermediates are difficult to prepare and involve in many steps.

The resolution of sulfoxide compounds including racemic omeprazole were described in WO 2004/002982. The method requires expensive reagents like titanium compounds, two chiral reagents namely diethyl-D-tartarate and L-Mandelic acid.

Enantioselective synthesis is described for example in Euro. J. Biochem. 166 (1987) 453 and U.S. Pat. No. 5,948,789. Disadvantages of these methods are that strict control of conditions is to be maintained and strict control of quantities of oxidizing agents is required for avoiding oxidation of desired sulfoxide to sulfone impurity. Moreover, these methods require expensive reagents like titanium isoproxide and diethyl-D-tartarate.

We have discovered a novel process for preparing substituted sulfoxides either as a single enantiomer or in an enantiomerically enriched form using less expensive reagents. The novel method provides a simple, straightforward and commercially viable process and overcomes above said drawbacks of the known processes.

SUMMARY OF THE INVENTION

The present invention provides a novel process for preparing a sulfoxide of formula I or a salt thereof either as a single enantiomer or in an enantiomerically enriched form:

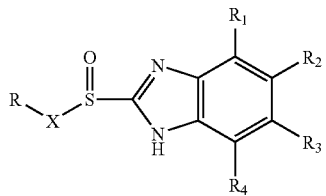

Wherein
R is

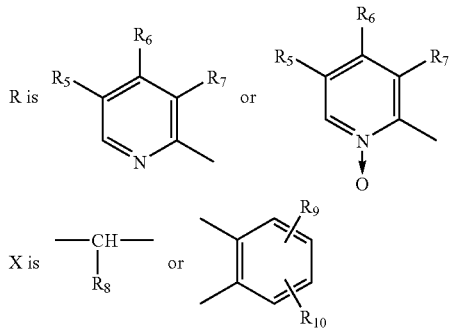

and $R_1$-$R_4$ are the same or different and selected from hydrogen, alkyl, alkoxy, halogen, halo-alkoxy, alkylcarbonyl, alkoxycarbonyl, oxazolyl, trifluroalkyl, or adjacent groups $R_1$-$R_4$ form ring structures which may be further substituted;

wherein $R_5$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

$R_6$ is selected from hydrogen, alkyl, alkylthio, alkoxy optionally substituted by fluorine, alkoxyalkoxy, dialkylamino, piperidino, morpholino, halogen, nitro, phenylalkyl and phenylalkoxy;

$R_8$ is hydrogen or forms an alkylene chain together with $R_7$ and $R_9$ and $R_{10}$ are same or different and selected from hydrogen, halogen and alkyl;

which comprises:

a) reacting a mixture of enantiomers of sulfoxide of formula II, differing in configuration at sulfur atom of sulfoxide or a salt thereof:

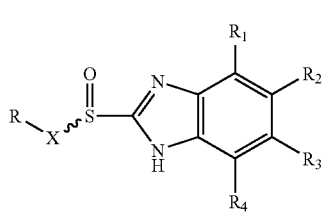

wherein R, X and $R_1$-$R_4$ are as defined for formula I;

with a chiral compound of formula III:

R*-Z-Y                                                                III wherein R* is a chiral moiety having at least one asymmetric center and at least one asymmetric center in the chiral moiety can have either R or S configuration;

Z is

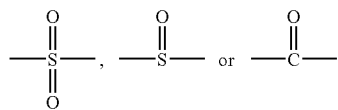

and Y is a leaving group to provide a mixture of diastereomeric compounds of formula IV:

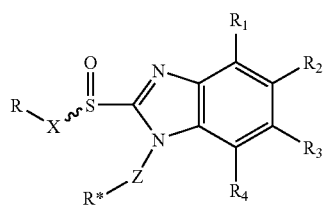

wherein R, X, R*, $R_1$-$R_4$ and Z are as defined above;

b) separating the diastereomers of formula IV; and c) deprotecting the separated diastereomers with an acid or base to provide a single enantiomer or enantiomerically enriched compound of formula I and optionally converting the enantiomer formed to the salt.

The compounds of formula IV as diastereomeric mixture or as individual diastereomers including their salts are novel and are also part of the invention.

In the above definitions alkyl groups, alkoxy groups and moieties thereof may be branched or straight $C_1$-$C_9$-chains or comprise cyclic alkyl groups, for example cyclicalkylalkyl.

DETAILED DESCRIPTION OF THE INVENTION

The present invention provides a novel process for preparing a sulfoxide of formula I or a salt thereof either as a single enantiomer or in an enantiomerically enriched form:

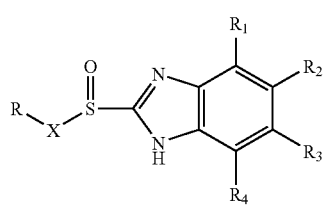

Wherein R is

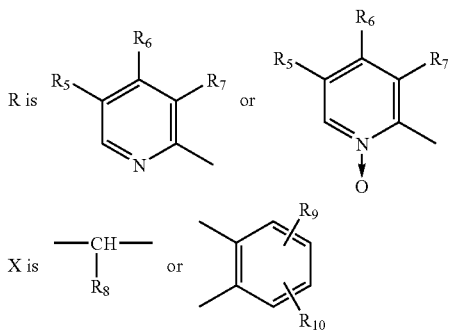

and $R_1$-$R_4$ are the same or different and selected from hydrogen, alkyl, alkoxy, halogen, halo-alkoxy, alkylcarbonyl, alkoxycarbonyl, oxazolyl, trifluroalkyl, or adjacent groups $R_1$-$R_4$ form ring structures which may be further substituted;

wherein $R_5$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

$R_6$ is selected from hydrogen, alkyl, alkylthio, alkoxy optionally substituted by fluorine, alkoxyalkoxy, dialkylamino, piperidino, morpholino, halogen, nitro, phenylalkyl and phenylalkoxy;

$R_8$ is hydrogen or forms an alkylene chain together with $R_7$ and $R_9$ and $R_{10}$ are same or different and selected from hydrogen, halogen and alkyl.

Except otherwise states, alkyl groups, alkoxy groups and moieties thereof may be branched or straight $C_1$-$C_9$-chains or comprise cyclic alkyl groups, for example cyclicalkylalkyl.

The wavy bond refers to both (R)- and (S)-configurations at the sulfur atom of the sulfoxide group.

Preferably, the sulfoxides prepared by the novel method are sulfoxides of formula I' or a salt thereof either as a single enantiomer or in an enantiomerically enriched form:

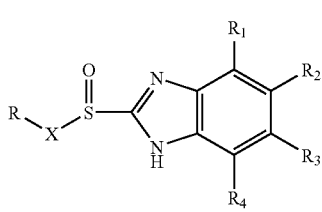

Wherein R is

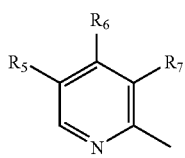

$R_6$ is selected from hydrogen, alkyl, alkylthio, alkoxy optionally substituted by fluorine, alkoxyalkoxy, dialkylamino, piperidino, morpholino, halogen, phenylalkyl and phenylalkoxy; and $R_1$- $R_5$, $R_7$- $R_{10}$ and X are as defined for formula I.

More preferably the sulfoxides prepared by the novel process are sulfoxides of any of the formulas I(i) to I(vi) or a salt thereof either as a single enantiomer or in an enantiomerically enriched form:

I(i)
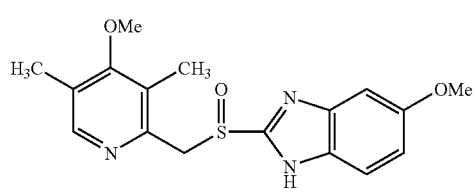

I(ii)
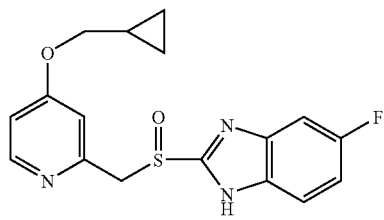

I(iii)
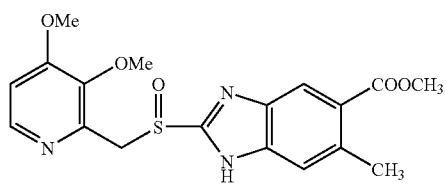

I(iv)
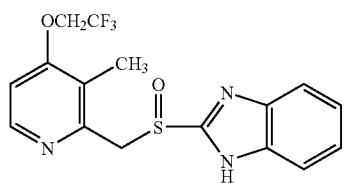

I(v)
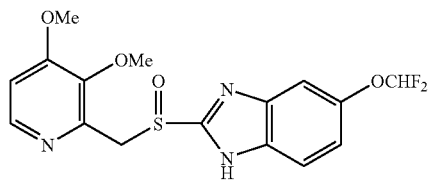

I(vi)
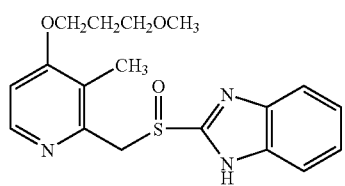

The compounds defined by the formulas I, I' and I(i-vi) may be converted to pharmaceutically acceptable salts by conventional methods.

Most preferably the sulfoxide prepared by the novel process is sulfoxide of the formula I(i) or a salt thereof either as a single enantiomer or in an enantiomerically enriched form.

According to the present invention initially a mixture of enantiomers of sulfoxide of formula II, differing in configuration at sulfur atom of sulfoxide or a salt thereof:

II
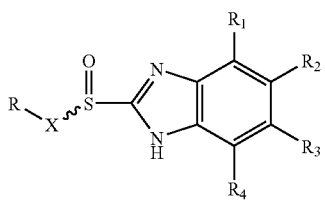

is reacted with a chiral compound of formula III:

R*-Z-Y          III to provide diastereomeric compounds of formula IV:

IV
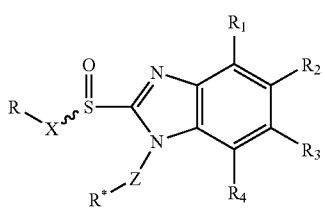

In the formulas II-IV, R, X, and $R_1$- $R_4$ have the same meaning as defined for formula I; R* is a chiral moiety having at least one asymmetric center and at least one asymmetric center in the chiral moiety can have either R or S configuration; Z is

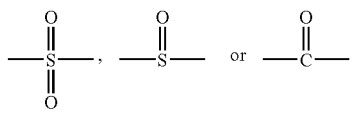

and Y is a leaving group such as halogen, hydroxy or reactive esterified hydroxy.

The salts of the compounds of formula II used in the reaction may be inorganic or organic salts. The preferable inorganic salts are alkali salts or alkaline earth metal salts. Preferred alkali metal salt of the compounds of formula II is lithium, sodium or potassium, more preferred being sodium or potassium metal salt. Preferred alkaline earth metal salt of the compounds of formula II is calcium or magnesium, more preferred being magnesium metal salt. The preferred organic salts of the compounds of formula II are organic ammonium salts, more preferred being tert-butylammonium salt, tetrabutylammonium salt and guanidinium salt.

The preferred Z is sulfonyl group:

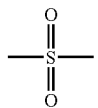

R* may or may not has aryl substitutions such as phenyl or hetero aryl substitutions such as pyridine on its chiral moiety. Preferably, R*-Z- is selected from (S) or (R) -camphor sulfonyl, (S)- or (R)-glycidylsulfonyl-, D- or L-mandeloyl, a stereo isomeric 1-(ethoxycarbonyl)-3-phenylpropyl]alanyl, (D) or (L)-phenyl alanyl and (D) or (L)-alanyl.

Preferably, reactive esterified hydroxy group is acetoxy or trifluoroacetoxy.

Halogen represents F, Cl, Br or I.

Preferably, Y is halogen, more preferably Cl or Br, still more preferably Cl.

Preferably, the reaction between the mixture of enantiomers of compound of formula II and the optically active compound of formula III is carried out in a solvent. Suitable solvents that can be used are esters such as ethyl acetate, methyl acetate, isopropyl acetate, tert-butyl methyl acetate and ethyl formate; alcohols such as methanol, ethanol and isopropyl alcohol; acetonitrile; tetrahydrofuran; dimethylformamide; dimethylsulfoxide; dioxane; aromatic hydrocarbons such as benzene, toluene, xylene, etc.; halogenated hydrocarbons such as methylene chloride, chloroform, carbontetrachloride, ethylene dichloride, etc.; ketones such as acetone, methyl ethyl ketone, methyl isobutyl ketone, diethyl ketone etc.; ethers such as tert-butyl methyl ether, diethyl ether; diethyl carbonate and a mixture thereof. Preferable solvents are selected from halogenated hydrocarbon solvents and aromatic hydrocarbon solvents, still more preferred solvents are methylene chloride, ethylenedichloride, toluene, benzene and xylene.

Preferably the reaction is carried out in the presence of a base such as N,N-diisopropylethylamine, triethyl amine or sodium carbonate.

The diastereomers of formula IV formed may be isolated from the reaction media and then used in the next step; or used directly in the next step.

The diastereomers of formula IV formed above are then separated. It is well known that diastereomers differ in their properties such as solubility and they can be separated based on the differences in their properties. The separation of the diastereomers can be performed using the methods known to the person skilled in the art. These methods include chromatographic techniques and fractional crystallization, preferable method being fractional crystallization.

Preferably, a solution of the diastereomeric mixture is subjected to fractional crystallization. The solution of the diastereomeric mixture may be a solution of the reaction mixture obtained as above or a solution prepared by dissolving the isolated diastereomeric mixture in a solvent. Any solvent may be used so long as it can be used for the separation. The preferred solvent is selected from alcohols such as methanol, ethanol and isopropyl alcohol, propanol, tert-butylalcohol, n-butanol; ketones such as acetone, methyl ethyl ketone, methyl isobutyl ketone, diethyl ketone; esters such as ethyl acetate, methyl acetate, isopropyl acetate, tert-butyl methyl acetate and ethyl formate; acetonitrile; tetrahydrofuran; dimethylformamide; dimethylsulfoxide; dioxane; diethyl carbonate and a mixture thereof. Water may also be associated with the above solvents. Preferable solvents are alcohol and ketone solvents, still more preferred solvents are alcohol solvents such as isopropyl alcohol and ethanol.

Fractional crystallization of preferentially one diastereomer from the solution of mixture of diastereomers can be performed by conventional methods such as cooling, partial removal of solvents, seeding or a combination thereof.

Fractional crystallization can be repeated until the desired chiral purity is obtained. But, usually one or two crystallizations may be sufficient.

The separated diastereomer of formula IV is then deprotected to provide sulfoxide of formula I either as a single enantiomer or in an enantiomerically enriched form. The deprotection can be applied to the sepereated diastereomers to get respective enantiomers.

The single enantiomer or the enantiomerically enriched enantiomer can be isolated from the reaction mixture or it can be isolated as a salt. The salts of the sulfoxide enantiomers can be prepared by conventional means. Optionally the enantiomers or salts thereof can be converted into pharmaceutically acceptable salts by conventional methods.

The deprotection can be performed by using an acid or a base. The selection of the acid or base is not critical. The acid can be an organic or inorganic. Acids such as carboxylic acids, e.g. acetic acid, formic acid; sulfonic acids, e.g. methane sulfonic acid; mineral acids such as phosphoric acid can be used.

The deprotection is preferably carried out with a base. The base can be an organic or inorganic. Preferable organic base is an amine. The amine may be primary, secondary or tertiary amine. The more preferred amine is triethyl amine or N,N-diisopropylethylamine.

The preferable inorganic bases are hydroxides, carbonates, bicarbonates, alkoxides and oxides of alkali or alkaline earth metals. The preferred alkali metal compounds are those of lithium, sodium and potassium, more preferred being those of sodium and potassium. The preferred alkaline earth metal compounds are those of calcium and magnesium more preferred being those of magnesium. Some example of these bases are sodium hydroxide, potassium hydroxide, magnesium hydroxide, magnesium oxide, sodium carbonate, potassium carbonate, sodium bicarbonate, potassium bicarbonate, sodium tert.butoxide and potassium tert.butoxide. The more preferred bases are hydroxides of sodium and potassium.

The deprotection may be carried out by contacting the separated diastereomer or a salt thereof with the base preferably in the presence of a solvent.

Suitable solvents that can be used in the deprotection are esters such as ethyl acetate, methyl acetate, isopropyl acetate, tert-butyl methyl acetate and ethyl formate; alcohols such as methanol, ethanol and isopropyl alcohol; acetonitrile; tetrahydrofuran; dimethylformamide; dimethylsulfoxide; dioxane; aromatic hydrocarbons such as benzene, toluene, xylene, etc.; halogenated hydrocarbons such as methylene chloride, chloroform, carbontetrachloride, ethylene dichloride, etc.; ketones such as acetone, methyl ethyl ketone, methyl isobutyl ketone, diethyl ketone etc.; ethers such as tert-butyl methyl ether, diethyl ether; diethyl carbonate and a mixture thereof. Preferable solvents are alcohol and ketone solvents, still more preferred solvents are alcohol solvents such as methanol, isopropyl alcohol and ethanol.

The enantiomers of compounds of formula I are either inhibitors of gastric acid secretion or intermediates for preparing them. These intermediates can be converted to the members of inhibitors of gastric acid secretion. For instant if $R_6$ of an enantiomer of the compound of formula I is nitro group then nitro can be replaced by methoxy group using sodium methoxide to obtain another member of the formula I. Similarly if R of an enantiomer of the compound of formula I is

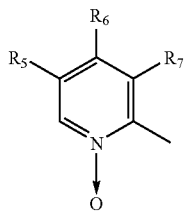

the N-oxide group can be reduced to pyridine compound by known methods to obtain another member of formula I.

The compounds of formula IV as diastereomeric mixture or as individual diastereomers including their salts are novel and are also part of the invention.

The process of the invention can also be used with promising results for optical purification of optically impure enantiomer of a sulfoxide of formula I.

(S)-5-Methoxy-2-[(3,5-dimethyl-4-methoxy-2-pyridyl)methylsulfinyl]1-H-benzimidazole ((S)-Omeprazole or Esomeprazole) or a salt thereof is the most preferred compound of the formula I. The preferred process for preparing esomeprazole or the salt can be shown in the scheme:

Scheme :

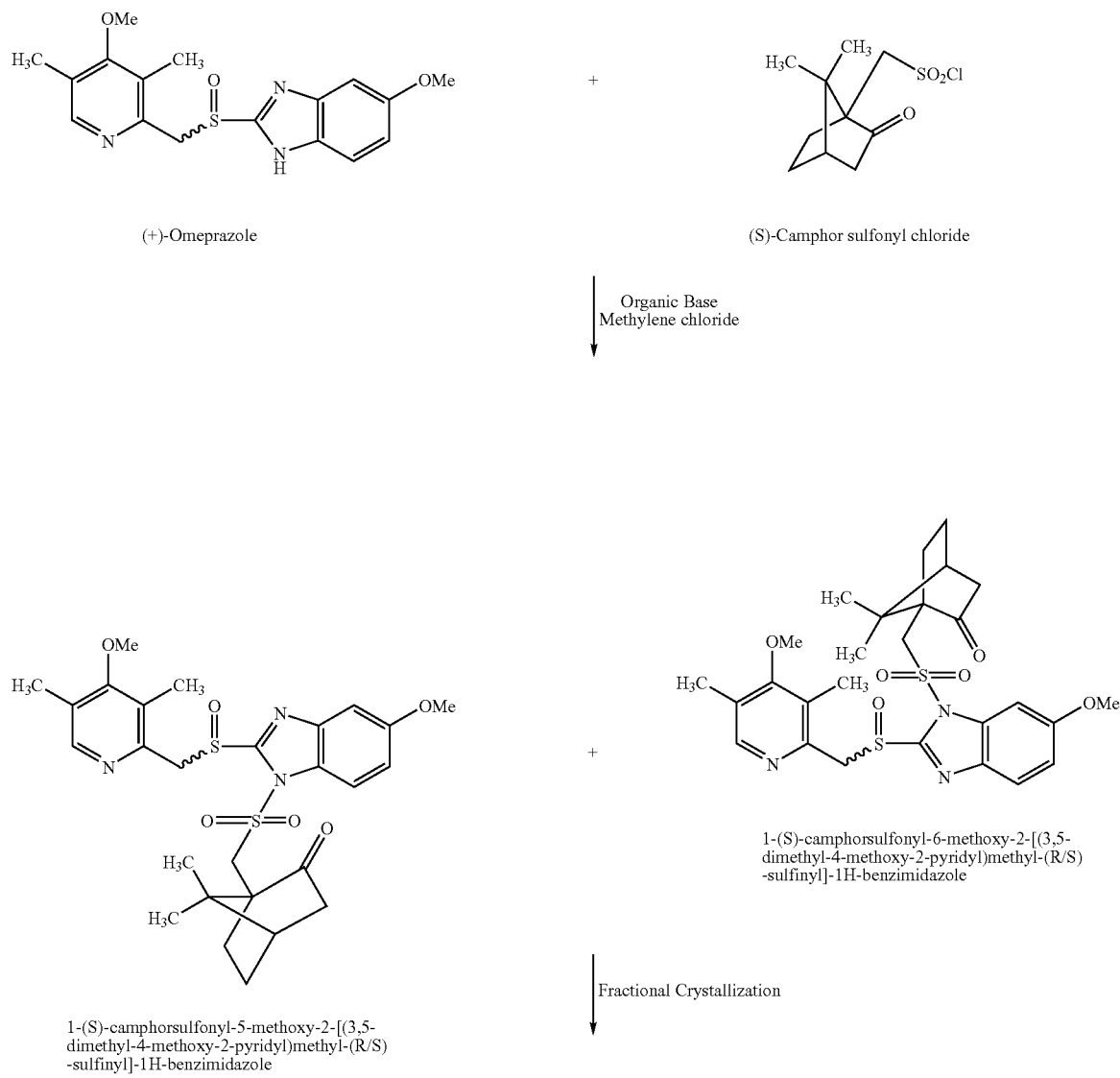

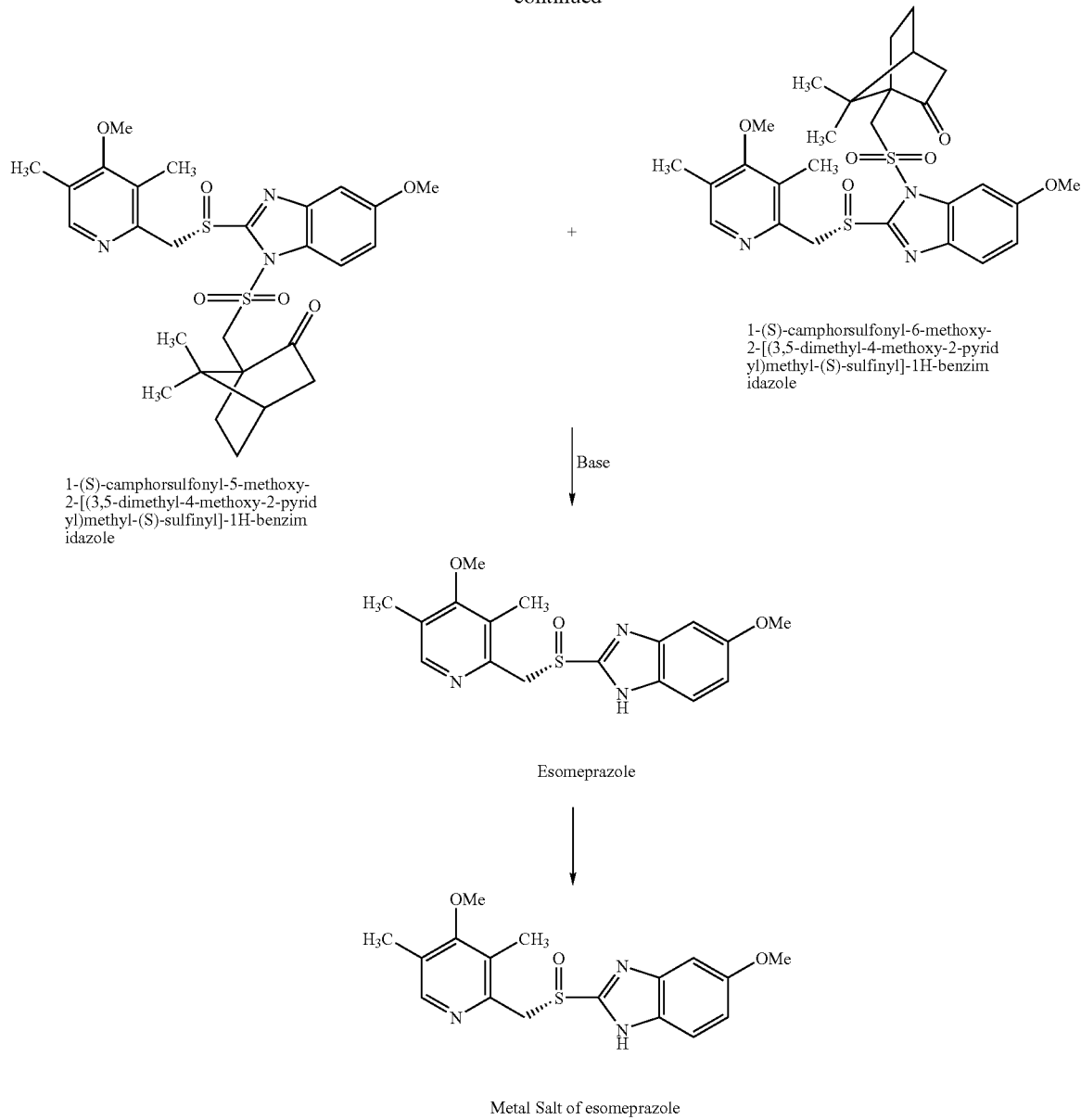

The diastereomers formed by reaction between racemate of 5-Methoxy-2-[(3,5-dimethyl-4-methoxy-2-pyridyl)methylsulfinyl]1-H-benzimidazole((±)-omeprazole) and (S)-camphor sulfonyl chloride results in the formation of a diastereomeric mixture of 1-(S)-camphor sulfonyl-(5-and 6)-methoxy-2-[(3,5-dimethyl-4-methoxy-2-pyridyl)methyl-(R/S)-sulfinyl]-1H-benzimidazole. From the mixture of 5- and 6-methoxy-benzimidazoles thus obtained, those with one configuration at the sulfur atom of sulfoxide group are separated from those with the opposite configuration, followed by the deprotection to give esomeprazole.

The formation of such 5- and 6-substituted benzimidazole are common for example as mentioned in U.S. Pat. No. 5,714,504 and where applicable such a substituted diastereomers of the compounds of formula IV and the formation of such substituted diastereomers of the compounds of formula IV are also part of the invention.

The following examples are given for the purpose of illustrating the present invention and should not be considered as limitations on the scope or spirit of the invention.

EXAMPLE 1

Racemate of 5-Methoxy-2-[(3,5-dimethyl-4-methoxy-2-pyridyl) methylsulfinyl]1-H-benzimidazole (15 gm) was dissolved in dichloromethane (150 ml) and N,N-diisopropylethylamine (8.5 gm) was added to the solution. The solution was cooled to 0-5° C. (S)-Camphor sulfonyl chloride (13.3 gm) dissolved in 25 ml of methylenechloride was added slowly for one hour at 0° C.-5° C. The reaction mixture was maintained at 0° C.-5° C. for 3 hours. The pH was adjusted to 6.0-6.5 with acetic acid, then ice-cooled water (60 ml) was added. The layers were separated. The organic layer was washed with 10% aqueous sodium chloride. The organic layer was distilled under reduced pressure to obtain a residue containing the diastereomeric mixture of 1-(S)-camphor sulfonyl-5-methoxy-2-[(3,5-dimethyl-4-methoxy-2-pyridyl)methyl-(R/S)-sulfinyl]-1H-benzimidazole and 1-(S)-camphor sulfonyl-6-methoxy-2-[(3,5-dimethyl-4-methoxy-2-pyridyl)methyl-(R/S)-sulfinyl]-1H-benzimidazole (23 gm).

EXAMPLE 2

The residue (23 gm) obtained as in example 1 was stirred with isopropyl alcohol (60 ml) for 2 hours at 25° C. and then refluxed for 1 hour. The solution was cooled to 25° C. and maintained for 3 hours. The solid obtained was collected by filtration. The solid was stirred in methanol (90 ml) for 30 min and filtered to obtain a mixture of 1-(S)-camphor sulfonyl-5-methoxy-2-[(3,5-dimethyl-4-methoxy-2-pyridyl)methyl-(S)-sulfinyl]-1H-benzimidazole and 1-(S)-camphor sulfonyl-6-methoxy-2-[(3,5-dimethyl-4-methoxy-2-pyridyl)methyl-(S)-sulfinyl]-1H-benzimidazole (8.1 gm).

EXAMPLE 3

Methanol (150 ml) was added to the product (8.1 gm) obtained as in example 2 and stirred for 30 min at 25° C., then sodium hydroxide solution (2.5 gm in 10 ml water) was added slowly for 10 min. The contents were stirred for 3 hours at 25° C. Then methanol was distilled off to obtain a residue. To the residue was added water (50 ml), the pH was adjusted to 6.8 with acetic acid and the product was extracted with methylenechloride. The layers were separated. The methylene chloride layer was washed with 5% aq. sodium chloride (50 ml), dried with sodium sulfate and the solvent was distilled to obtain 4.5 gm residue containing (S)-5-Methoxy-2-[(3,5-dimethyl-4-methoxy-2-pyridyl)methylsulfinyl]1-H-benzimidazole (Esomeprazole).

EXAMPLE 4

The residue (4.5 gm) obtained as in example 3 was dissolved in methanol (25 ml) at 25° C. and the solution was cooled to 5-10° C. Potassium hydroxide solution in methanol (1.5 gm in 8 ml methanol) was added slowly for 30 min. During addition of potassium hydroxide solution, solid was thrown out. The temperature was raised to 25° C., stirred for 14 hours, filtered and dried to obtain 4.5 gm of potassium salt of (S)-5-Methoxy-2-[(3,5-dimethyl-4-methoxy-2-pyridyl)methylsulfinyl]1-H-benzimidazole (Esomeprazole potassium) (Eantiomeric excess: 99.6%).

EXAMPLE 5

Potassium salt of (S)-5-Methoxy-2-[(3,5-dimethyl-4-methoxy-2-pyridyl) methylsulfinyl]1-H-benzimidazole (Esomeprazole potassium) (5.2 gm) was dissolved in water (75 ml). To this solution, was added magnesium chloride solution (1.4 gm in 50 ml water), and then the contents were stirred for 1 hour at 25° C. The solid precipitated was filtered, washed with water and dried under vacuum for 12 hours at 40° C. to obtain 4.0 gm of esomeprazole magnesium dihydrate (enantiomeric excess: 99.7%).

EXAMPLE 6

Magnesium (0.18 gm) was dissolved in methanol (50 ml) and dichloromethane (0.5 ml) was added. The reaction mass was stirred at 25° C. for 5 hours under nitrogen. Then esomeprazole (3.0 gm) obtained as in example 3 was added and stirred for 12 hours. Water (20 ml) was added to reaction mass and stirred for 15 minutes. The precipitated solid was filtered and the solid was recrystallized from acetone and methanol to obtain 2.5 gm of esomeprazole magnesium dihydrate (enantiomeric excess: 99.6%, optical rotation:−128° (c=0.5% methanol)).

We claim:

1. A compound of formula IV:

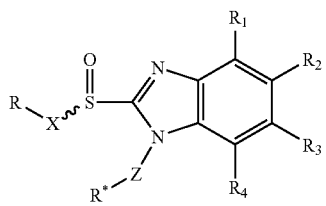

wherein

R is

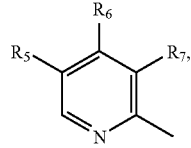

X is

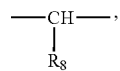

and

R*-Z- is (S)-camphor sulfonyl or (R)-camphor sulfonyl;

$R_1$, $R_2$, $R_3$, and $R_4$ are the same or different and each independently selected from H, F, methyl, methoxy, difluoromethoxy, methoxycarbonyl;

$R_5$ and $R_7$ are the same or different and each independently selected from H, methyl, methoxy; and $R_6$ is selected from methoxy, methoxypropoxy, trifluoroethoxy and cyclopropylmethoxy; and $R_8$ is hydrogen.

2. The compound of claim 1, wherein the compound of formula IV is a mixture of diastereomers.

3. The compound of claim 2, wherein the compound of formula IV is a diastereomer.

4. The compound of claim 1, wherein the R*-Z- is (R)-camphor sulfonyl.

5. The compound of claim 1, wherein the R*-Z- is (S)-camphor sulfonyl.

* * * * *